US010675056B2

(12) United States Patent
Tokarz

(10) Patent No.: US 10,675,056 B2
(45) Date of Patent: Jun. 9, 2020

(54) ACCESS APPARATUS WITH INTEGRATED FLUID CONNECTOR AND CONTROL VALVE

(71) Applicant: Covidien LP, Mansfield, MA (US)

(72) Inventor: Christopher Tokarz, Torrington, CT (US)

(73) Assignee: Covidien LP, Mansfield, MA (US)

( * ) Notice: Subject to any disclaimer, the term of this patent is extended or adjusted under 35 U.S.C. 154(b) by 39 days.

(21) Appl. No.: 16/106,871

(22) Filed: Aug. 21, 2018

(65) Prior Publication Data

US 2019/0069925 A1 Mar. 7, 2019

Related U.S. Application Data

(60) Provisional application No. 62/555,231, filed on Sep. 7, 2017.

(51) Int. Cl.
*A61B 17/34* (2006.01)
*A61B 17/02* (2006.01)

(52) U.S. Cl.
CPC ...... *A61B 17/3423* (2013.01); *A61B 17/3474* (2013.01); *A61B 17/3498* (2013.01); *A61B 17/0218* (2013.01); *A61B 17/3421* (2013.01); *A61B 17/3462* (2013.01); *A61B 2017/3449* (2013.01)

(58) Field of Classification Search
CPC ............ A61B 17/3423; A61B 17/3421; A61B 17/3462; A61B 17/3498
See application file for complete search history.

(56) References Cited

U.S. PATENT DOCUMENTS

| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |

(Continued)

FOREIGN PATENT DOCUMENTS

| CA | 2702419 A1 | 11/2010 |
| EP | 0226026 A2 | 6/1987 |

(Continued)

OTHER PUBLICATIONS

Extended European Search Report issued in European Application No. 18192877.1 dated Dec. 14, 2018, 9 pages.

*Primary Examiner* — Julianna N Harvey
(74) *Attorney, Agent, or Firm* — Carter, DeLuca & Farrell, LLP

(57) ABSTRACT

An access apparatus includes an access housing, an access member extending from the access housing, a fluid connector mounted to the access housing and a control valve mounted to the fluid connector. The control valve is positionable relative to the fluid connector between a first position corresponding to a desufflation operative state permitting rapid desufflation of the underlying body cavity, a second position corresponding to an insufflation operative state permitting insufflation fluid flow into the access member and into the underlying body cavity, and a third position corresponding to a closed operative state.

13 Claims, 4 Drawing Sheets

(56) References Cited

U.S. PATENT DOCUMENTS

| | | |
|---|---|---|
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,812 A * | 2/1999 | Correia ............... A61B 17/3498 604/167.01 |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,036,711 A | 3/2000 | Mozdzierz et al. |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |

(56) References Cited

U.S. PATENT DOCUMENTS

| | | |
|---|---|---|
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |

(56) References Cited

U.S. PATENT DOCUMENTS

| | | |
|---|---|---|
| 8,585,632 B2 | 11/2013 | Okoniewski |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111052 A1 | 6/2004 | Moenning |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0047185 A1 | 3/2006 | Shener et al. |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |

(56) References Cited

U.S. PATENT DOCUMENTS

| | | |
|---|---|---|
| 2013/0274559 A1 | 10/2013 | Fowler et al. |
| 2013/0310651 A1 | 11/2013 | Alfieri |
| 2014/0018632 A1 | 1/2014 | Kleyman |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |

* cited by examiner

ACCESS APPARATUS WITH INTEGRATED FLUID CONNECTOR AND CONTROL VALVE

CROSS-REFERENCE TO RELATED APPLICATIONS

This application claims the benefit of and priority to U.S. Provisional Patent Application Ser. No. 62/555,231 filed Sep. 7, 2017, the entire disclosure of which is incorporated by reference herein.

BACKGROUND

1. Technical Field

The present disclosure relates to an access apparatus and, more particularly, relates to an access apparatus including an integrated fluid connector and valve for controlling flow of insufflation fluids during a laparoscopic procedure.

2. Description of Related Art

In laparoscopic procedures, clinicians perform surgery in the interior of the abdomen through one or more narrow tubes or cannulas inserted through small entrance openings or incisions in the skin. In certain instances, an insufflation port associated with one cannula provides a pressurized gas, e.g., $CO_2$, into the abdominal cavity after the cannula is inserted into the entrance opening and secured to a patient, thus creating or maintaining a pneumoperitoneum. The gas provides positive pressure raising the inner abdominal wall from internal organs, thereby providing the clinician with an operating space in which a surgical procedure is performed. By creating the operating space, the clinician avoids contact with the organs while the instruments are manipulated within the cannulas.

A conventional cannula typically includes a luer connector and stop cock valve to control flow of insufflation fluids. The cannula also may incorporate a seal system having an object seal for establishing a seal about a surgical object, e.g., a surgical instrument, introduced through the cannula, and a zero-closure valve for preventing release of the pressurized gas through the cannula in the absence of the surgical object. In some of the larger diameter cannulas, the seal system may be detachable relative to the cannula, which assists in release of the insufflation gases from the abdomen subsequent to performance of the procedure.

SUMMARY

Accordingly, the present disclosure is directed to improvements in controlling entry and exit of insufflation fluids through an access apparatus such as a cannula, particularly, a cannula of relatively small diameter, e.g., 5 millimeters (mm) or less and devoid of a removable seal system. In one embodiment, an access apparatus includes an access housing, an access member extending from the access housing, a fluid connector mounted to the access housing and a control valve. The access housing and the access member define a central longitudinal axis and a longitudinal opening for passage of a surgical object. The fluid connector includes a valve chamber segment and a coupler segment depending radially outwardly relative to the valve chamber segment. The fluid connector defines a fluid passage extending through at least the valve chamber segment and the coupler segment. The valve chamber segment defines a chamber exit port in fluid communication with the fluid passage. The coupler segment is configured for coupling to an insufflation fluid source. The control valve includes a valve stem at least partially positioned within the valve chamber segment. The valve stem includes a valve channel extending through the valve stem and a valve intake port in fluid communication with the valve channel. The control valve is selectively positionable between a first position corresponding to a desufflation operative state where the valve intake port is in fluid communication with the access member and the valve channel is in fluid communication with the chamber exit port of the fluid connector to thereby permit exit of the insufflation fluids relative to the access member, a second position corresponding to an insufflation operative state where the valve channel is in fluid communication with the fluid passage of the fluid connector to permit passage of insufflation fluids from the insufflation fluid source to the access member, and a third position corresponding to a closed operative state where the valve stem intersects the fluid passage to prevent egress of insufflation fluids from the access member, and maintain, e.g., a pneumoperitoneum.

In embodiments, the control valve is configured to rotate about an axis of rotation between the first, second and third positions. In some embodiments, the axis of rotation is parallel to the central longitudinal axis of the access member.

In certain embodiments, the valve channel of the control valve is linear and is arranged about a valve channel axis. In embodiments, the valve intake port is configured to intersect the valve channel and is arranged about a valve intake port axis. In some embodiments, the valve stem includes a closed side opposing the valve intake port along the valve intake port axis. In embodiments, the closed side of the valve stem is positioned radial outward of the chamber exit port of the fluid connector when in the first position of the control valve and intersects the flow passage of the fluid connector. In embodiments, the closed side of the valve stem is configured to close the chamber exit port of the valve chamber segment of the fluid connector when in the second position of the control valve. In some embodiments, the closed side of the valve stem is positioned radial inward of the chamber exit port when in the third position of the control valve and intersects the flow passage of the fluid connector.

In embodiments, the control valve includes a valve lever connected to the valve stem, and configured for manual manipulation and being selectively movable to move the control valve between the first, second and third positions.

In some embodiments, the fluid connector and the access housing are monolithically formed.

In certain embodiments, a closure element is mounted relative to the access housing. The closure element is configured to open upon introduction of the surgical object therethrough and close in the absence of the surgical object. In embodiments, the fluid passage of the fluid connector is in fluid communication with the longitudinal opening of the access housing and the access member distal of the closure element.

In one embodiment, an access apparatus includes an access housing, an access member extending from the access housing, a fluid connector mounted to the access housing and being configured for coupling to an insufflation fluid source, and a control valve at least partially positioned within the fluid connector. The access housing and the access member define a central longitudinal axis and have a longitudinal opening for passage of a surgical object. The fluid connector defines a fluid passage extending therethrough, and has an exit port in a side wall portion thereof in fluid communication with the fluid passage. The control valve defines a valve channel therethrough and a valve intake port in fluid communication with the valve channel. The control valve is selectively positionable between a first position corresponding to a desufflation operative state where the valve intake port is aligned with the fluid passage of the fluid connector and the flow channel is aligned with the exit port of the fluid connector to permit insufflation fluids to flow from the access member through the valve intake port for discharge through the valve channel and the exit port, a second position corresponding to an insufflation operative state where the valve channel is aligned with the fluid passage of the fluid connector to permit passage of insufflation fluids from the insufflation fluid source through the fluid passage to the access member, and a third position corresponding to a closed operative state where the control valve intersects the flow passage of the fluid connector to prevent egress of insufflation fluids from the access member.

In embodiments, the fluid connector and the access housing are monolithically formed. In some embodiments, the control valve is configured to rotate about an axis of rotation between the first, second and third positions whereby the axis of rotation is parallel to the central longitudinal axis of the access member.

The integrated fluid connector and control valve permits functioning of the apparatus between three operative states, namely, a desufflation, an insufflation and a closed operative state of operation. The fluid connector is integrally formed with the access housing and requires only one opening in its sidewall. The control valve in combination with the fluid connector permits rapid desufflation even in the absence of a removable seal system.

Other advantages of the present disclosure will be appreciated from the following description.

BRIEF DESCRIPTION OF THE DRAWING(S)

Embodiments of the present disclosure will be appreciated by reference to the accompanying drawings wherein.

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

The present disclosure has application in a variety of surgical access devices adapted for permitting percutaneous access to a target site. These access devices include, but are not limited to, trocars and/or cannulas, catheters, hand access devices, etc. The present disclosure is contemplated for use in various surgical procedures including, e.g., endoscopic, arthroscopic, thoracic, etc., but has particular application in a laparoscopic procedure performed in the abdominal cavity.

In the following description, as is traditional, the term "proximal" will refer to the portion of the instrument closest to the clinician while the term "distal" refers to the portion of the instrument most remote from the clinician.

Figure 1:
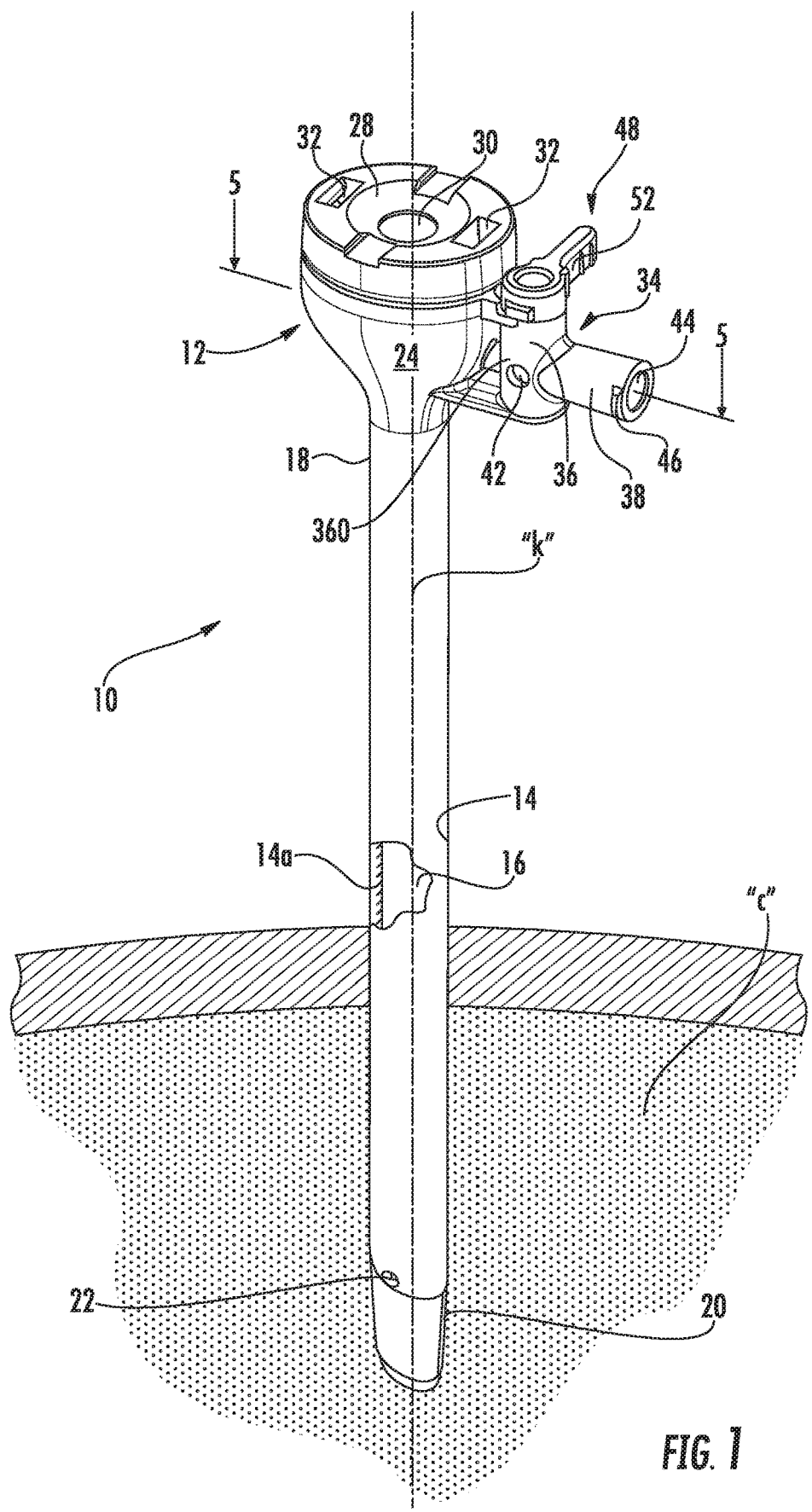
FIG. 1 is a perspective view of the surgical access apparatus in accordance with the present disclosure illustrating the access housing, the integrated fluid connector with the control valve mounted to the access housing, and the access member extending from the access housing.
Figure 2:
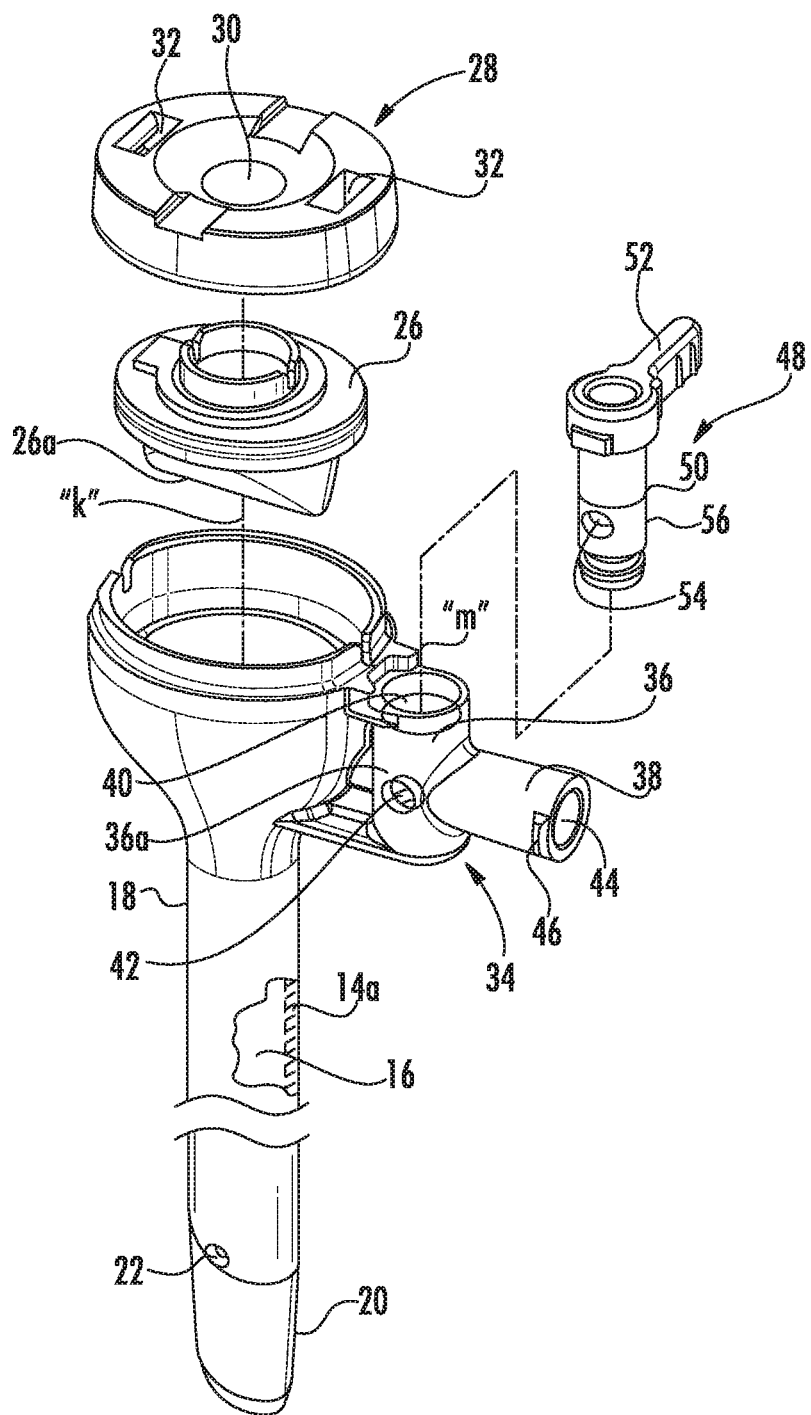
FIG. 2 is an exploded perspective view of the access apparatus.

Referring now to FIGS. 1-2, the access apparatus of the present disclosure is illustrated. The access apparatus 10 may be any member suitable for the intended purpose of accessing a body cavity and typically defines a passageway permitting introduction of instruments or the clinician's hand. The access apparatus 10 is particularly adapted for use in laparoscopic surgery where the abdominal or peritoneal cavity is insufflated with a suitable fluid or gas, e.g., $CO_2$, to raise the cavity wall from the internal organs therein. The access apparatus 10 is typically used with an obturator assembly (not shown) which may be blunt, a non-bladed, or a sharp pointed instrument positionable within the passageway of the access apparatus 10. The obturator assembly is utilized to penetrate the abdominal wall to introduce the access apparatus 10 through the abdominal wall, and then subsequently is removed from the access apparatus 10 to permit introduction of the surgical instrumentation utilized to perform the procedure through the passageway.

The access apparatus 10 includes an access housing 12 and an access member 14 coupled to the access housing 12. The access housing 12 and the access member 14 collectively define a longitudinal axis "k", and have a longitudinal opening 16 therethrough (cut-away portions of FIGS. 1-2). The access member 14 may be cylindrical along at least a portion of its length and defines proximal end segment 18 and distal end segment 20. The access number 14 may be a cannula dimensioned for introduction within the abdominal cavity "c", and may include a port opening 22 in its outer wall 14a in communication with the longitudinal opening 16 and adjacent the distal end segment 20 for passage or release of insufflation fluids. In the alternative, the access member 14 may include a separate tube or channel for passage of the insufflation fluids. The access member 14, in the form of a cannula, may range from 3 mm to 15 mm. In embodiments, the access member 14 has a diameter of 5 mm or less.

The access housing 12 includes a housing segment 24, a closure element 26 disposed within the housing segment 24 and a cover 28. The housing segment 24 and the access member 14 may be monolithically formed as a single unit, or may be separate components secured to each other through conventional means. The housing segment 24 defines a semi-hemispherical or elliptical shape which tapers radially inwardly in the distal direction relative to the longitudinal axis "k". The closure element 26 is a zero closure valve configured to open upon passage of the surgical object therethrough, and close in the absence of the surgical object and/or in response to pressure provided by the underlying insufflation fluids. The closure element 26 may be a duckbill valve defining a slit 26a which provides a passageway through the closure element 26. Other zero closure valves are also contemplated. The access housing 12 also may include an object seal (not shown) configured to establish a sealing relation about a surgical object or instrument introduced therethrough. Suitable object seals include septum seals, single slit seals, double slit seals or the like.

The cover 28 is secured to the housing segment 24 through conventional means to enclose the closure element 26 and the interior of the access apparatus 10. The cover 28 includes a central opening 30 which leads to the longitudinal opening 16. The cover 28 may include diametrically opposed openings 32 for receiving sutures (not shown) for securing the access apparatus 10 relative to the surgical site.

With continued reference to FIGS. 1-2, the access housing 12 further includes a fluid connector 34 depending radially outwardly from the outer surface of the housing segment 24. The fluid connector 34 is integral with the housing segment 24, and, in one embodiment, is monolithically formed with the housing segment 24. In the alternative, the fluid connector 34 may be a separate component secured to the housing segment 24 through a mechanical coupling, adhesive, etc. The fluid connector 34 includes a valve chamber segment 36 and a coupler segment 38 depending radially outwardly relative to the valve chamber segment 36. The valve chamber segment 36 is arranged around a chamber axis "m" (FIG. 2) which, in one embodiment, is in general parallel relation with the central longitudinal axis "k". The valve chamber segment 36 defines an internal chamber 40 having a generally cylindrical configuration, and a single chamber exit port 42 extending through a side wall portion 36a thereof and in fluid communication with the internal chamber 40. The coupler segment 38 defines a central flow bore 44 therethrough and has an external male thread 46 (e.g., a luer coupling) for coupling to tubing of an insufflation system or source of pressurized fluids.

Figure 3:
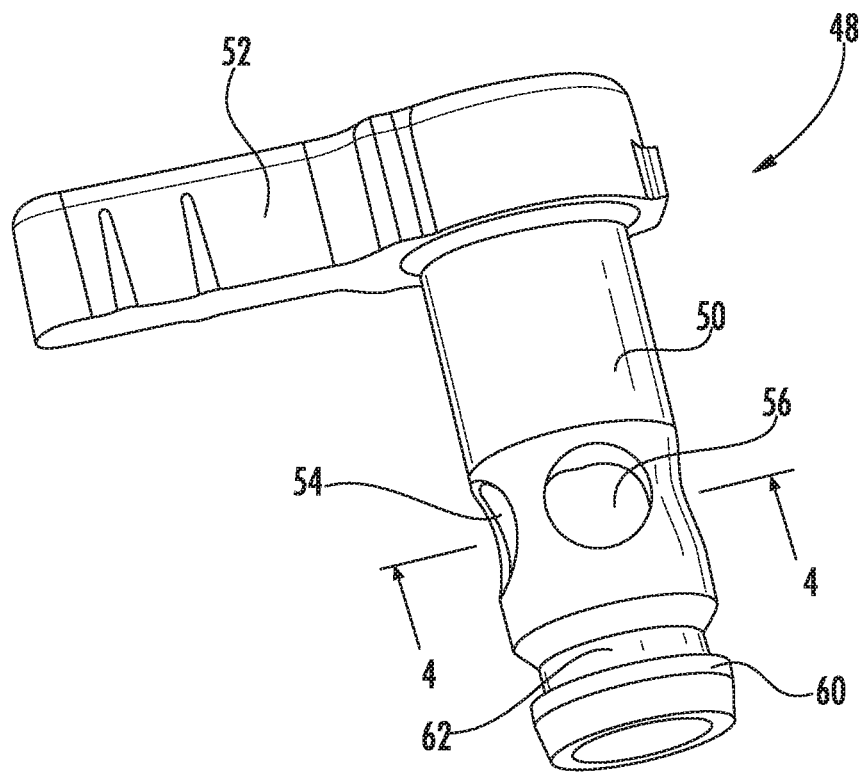
FIG. 3 is a first perspective view of the control valve of the access apparatus.
Figure 4:
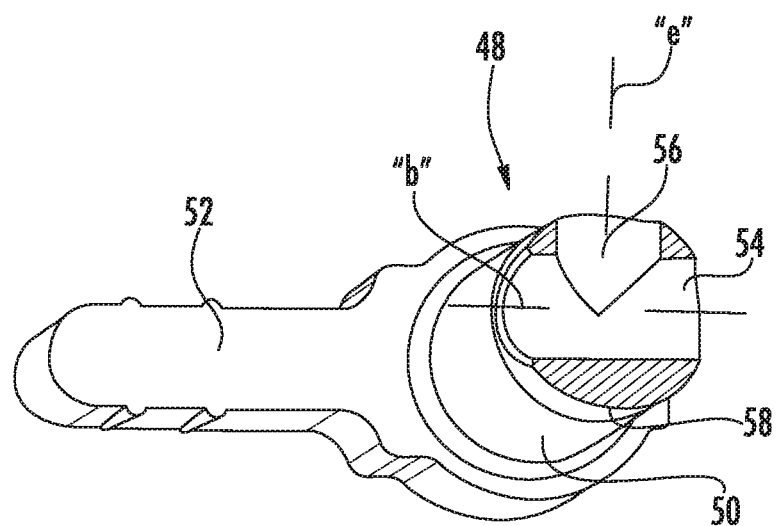
FIG. 4 is a second perspective view in partial cross-section of the control valve of the access apparatus.

Referring now to FIGS. 3-4, in conjunction with FIG. 2, the access apparatus 10 includes a flow control valve 48 positionable relative to the valve chamber segment 36 of the fluid connector 34. The control valve 48 includes a valve stem 50 and a valve lever 52 coupled to the valve stem 50. The valve lever 52 is configured for engagement by the clinician to move, e.g., rotate, the control valve 48 relative to the valve chamber segment 36. The valve stem 50 is generally cylindrical in cross-section and is received within the correspondingly dimensioned internal chamber 40 of the valve chamber segment 36. The valve stem 50 includes a linear valve channel 54 arranged about a valve channel axis "b" and extending completely through opposed sides of the valve stem 50 and a valve intake port 56 on one side of the valve stem 50 and in communication with the valve channel 54. (FIG. 4) The valve intake port 56 is arranged about a valve intake port axis "e". The valve stem 50 is closed on the side opposing the valve intake port 56 (e.g., along the valve intake port axis "e") thereby defining a closed side 58 of the valve stem 50 diametrically opposing the valve intake port 56. In one embodiment, the valve intake port 56 is oriented at a 90° interval relative to the valve channel 54 such that the valve intake port axis "e" of the valve intake port 56 is orthogonal to the valve channel axis "b" of the valve channel 54. Other orientations are also envisioned. The valve intake port 56 defines a smaller diameter than the diameter of the valve channel 54. The valve stem 50 further includes a mounting rib 60 adjacent its distal end which defines a mounting recess 62. The mounting rib 60 and/or the mounting recess 62 interact with corresponding structure (not shown) within the valve chamber segment 36 of the fluid connector 34 to secure the control valve 48 within the valve chamber segment 36.

The valve stem 50 can be cylindrical in shape with a valve channel that is linear and passes through the valve stem from a first side to a second side, opposite the first side. The intake port 56 is orthogonal to the valve channel and opposite the closed side 58, which is formed by a wall of the valve stem.

Figure 5:
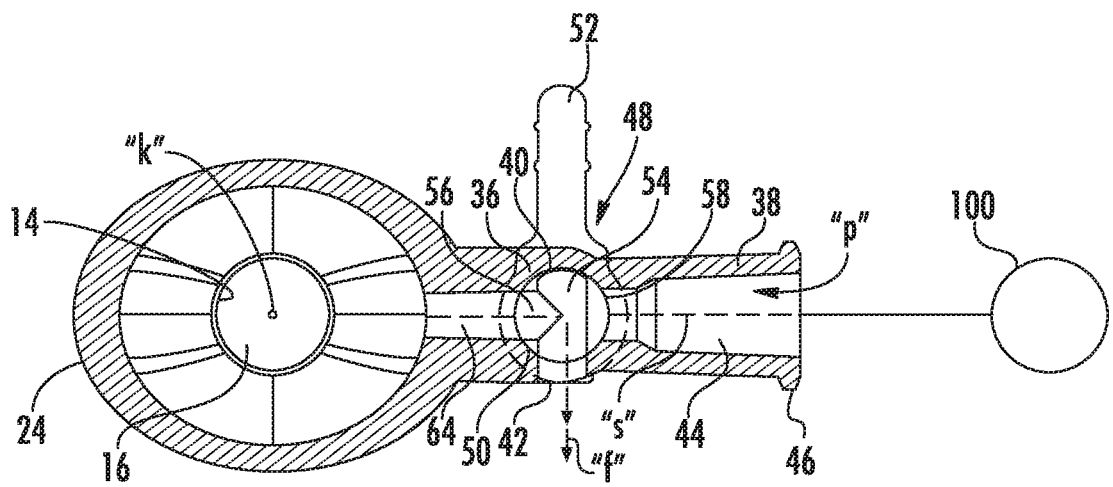
FIG. 5 is a cross-sectional view taken along the lines 5-5 of FIG. 1 illustrating a first position of the control valve corresponding to a desufflation operative state of the access apparatus.

FIG. 5 illustrates, in cross-section, the assembled access apparatus 10. In FIG. 5, the flow passage "p" extending through the fluid connector 34 is also depicted, and is inclusive of the flow bore 44 of the coupler segment 38, the internal chamber 40 of the valve chamber segment 36 and the intermediate flow bore 64 extending between the valve chamber segment 36 and the housing segment 24 of the access housing 12. The flow passage "p" permits fluid communication between the insufflation fluid source, schematically identified as reference numeral 100, and the interior of the housing segment 24 distal of the closure element 26. The flow passage "p" is generally arranged around flow axis "s" which, in one embodiment, is orthogonal to the central longitudinal axis "k". Other arrangements are also envisioned.

FIG. 5 also illustrates a first position of the control valve 48 corresponding to the desufflation operative state of the access apparatus 10. In the first position, the valve intake port 56 of the valve stem 50 is in alignment with the intermediate flow bore 64 of the fluid connector 34 thereby establishing fluid communication with the access member 14, and the valve channel 54 is in alignment with the chamber exit port 42 of the valve chamber segment 36. The closed side 58 of the valve stem 50 is in alignment with, and intersects, the flow bore 44 of the coupler segment 38 thereby closing the fluid passage "p" to the insufflation fluid source 100. The closed side 58 of the valve stem 50 is disposed radial outward of the chamber exit port 42. Thus, in the first position, the insufflation fluids "f" may be conveyed from the access member 14 and the housing segment 24 into the fluid connector 34 and passed through the valve intake port 56 and the valve channel 54 of the valve stem 50, to rapidly exit the chamber exit port 42 of the valve chamber segment 36.

Figure 6:
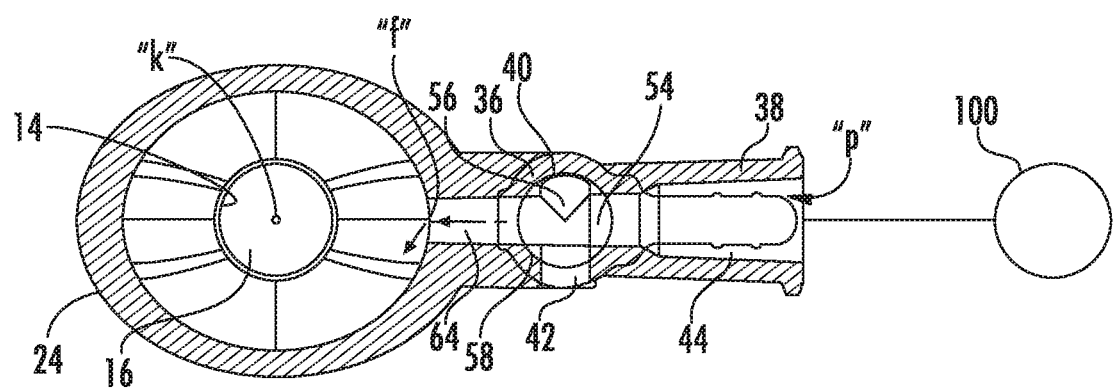
FIG. 6 is a cross-sectional view similar to the view of FIG. 5 illustrating a second position of the control valve corresponding to an insufflation operative state of the access apparatus.

FIG. 6 illustrates a second position of the control valve 48 corresponding to the insufflation operative state of the access apparatus 10. In the second position, the closed side 58 of the valve stem 50 intersects, blocks or covers the chamber exit port 42 of the valve chamber segment 36 while the valve channel 54 of the valve stem 50 is in alignment with the flow bore 44 of the coupler segment 38 thereby completely opening the flow passage "p" through the fluid connector 34. Thus, in the second position, the insufflation fluids "f" will pass from the insufflation fluid source 100 through the fluid connector 34 and into the housing segment 24 and/or access member 14 distal of the closure element 26 within the access housing 12.

Figure 7:
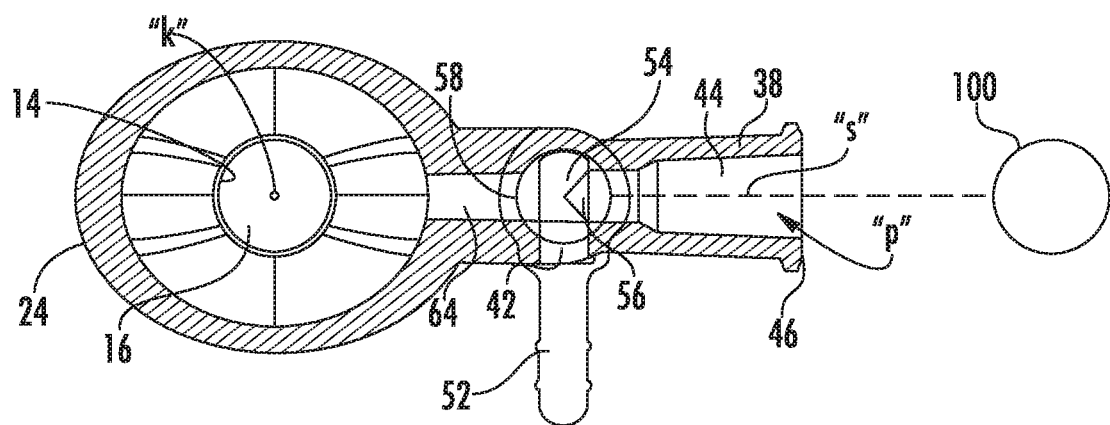
FIG. 7 is a cross-sectional view similar to the view of FIG. 5 illustrating a third position of the control valve corresponding to a closed operative state of the access apparatus.

FIG. 7 illustrates a third position of the control valve 48 corresponding to the closed operative state of the access apparatus 10. In the third position, the closed side 58 of the valve stem 50 is disposed radial inward of the chamber exit port 42, and is arranged to intersect or block the intermediate flow bore 64 of the fluid connector 34 thereby closing the fluid passage "p" of the fluid connector 34 relative to the access member 14, e.g. preventing egress of insufflation fluids "f" from the access member 14. In the third state, the pneumoperitoneum is maintained without passage of insufflation fluids between the insufflation fluid source 100 and the access member 14. The insufflation fluid source 100 also may be deactivated through, e.g., closing a valve associated with the insufflation fluid source 100 or turning the source to an off-mode of operation.

The use of the access apparatus 10 will now be discussed. The access apparatus 10 is introduced through the abdominal wall to access the underlying abdominal cavity. In accordance with one methodology, an obturator (not shown) is positioned within the access apparatus 10 and advanced through the abdominal wall, e.g., through a previously created incision in the abdominal wall or through an opening created by the obturator, to position at least the distal end segment 20 of the access member 14 within the abdominal cavity "c" as depicted in FIG. 1. Prior to accessing the abdominal cavity "c", the abdominal cavity "c" may be at least partially or fully expanded with insufflation fluids, $CO_2$, introduced via an insufflation needle to establish a pneumoperitoneum. A surgical object, e.g., a laparoscopic surgical instrument such as a grasper, scissor, electrosurgical device, stapler, etc. may be advanced through the access apparatus 10 and into the underlying surgical site to perform a surgical task. If, during the procedure, insufflation fluids are required to establish or maintain the pneumoperitoneum, the control valve 48 may be oriented to the position of FIG. 6 corresponding to the insufflation operative state thereby permitting passage of insufflation fluids from the insufflation fluid source 100 through the fluid connector 34 and into the access member 14 for delivery within the abdominal cavity "c". When the desired state of pneumoperitoneum is achieved, the control valve 48 may be manipulated to the position of FIG. 7 corresponding to the closed operative state which blocks egress of the insufflation fluids through the flow passage "p" of the fluid connector 34 and through the control valve 48. Upon completion of the surgery or when it is determined that rapid desufflation of the abdominal cavity is required, the control valve 48 is maneuvered to the first position depicted in FIG. 5 corresponding to the desufflation operative state, which aligns the valve intake port 56 of the valve stem 50 with the intermediate flow bore 64 of the fluid connector and aligns the valve channel 54 with the chamber exit port 42 of the valve chamber segment 36. Thus, in the first position, the insufflation fluids "f" may pass through the access member 14 and the access housing 12 into the fluid connector 34 through the valve intake port 56 and the valve channel 54 and rapidly exit the chamber exit port 42 of the valve chamber segment 36.

Thus, the integrated fluid connector 34 and control valve 48 of the present disclosure provides the ability of quick desufflation without requiring removal of a detachable seal system. Only one exit hole, chamber exit port 42, is required in the side wall of the fluid connector 34 and, in combination with the respective configurations of the valve channel 54 and the valve intake port 56 of the valve stem 50, permits ready transition between the three operative states of the access apparatus 10.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. An access apparatus, comprising:
an access housing;
an access member extending from the access housing, the access housing and the access member defining a central longitudinal axis and having a longitudinal opening for passage of a surgical object;
a fluid connector mounted to the access housing, the fluid connector including a valve chamber segment and a coupler segment depending radially outwardly relative to the valve chamber segment and the longitudinal axis, the fluid connector defining a fluid passage extending at least through the valve chamber segment and the coupler segment, the valve chamber segment defining a chamber exit port in fluid communication with the fluid passage, the coupler segment configured for coupling to an insufflation fluid source; and
a control valve including a valve stem at least partially positioned within the valve chamber segment, the valve stem including a valve channel extending through the valve stem and a valve intake port in fluid communication with the valve channel, the control valve selectively positionable between a first position corresponding to a desufflation operative state where the valve intake port is in fluid communication with the access member and the valve channel is in fluid communication with the chamber exit port of the fluid connector to thereby permit exit of the insufflation fluids relative to the access member, a second position corresponding to an insufflation operative state where the valve channel is in fluid communication with the fluid passage of the fluid connector and with the insufflation fluid source to permit passage of insufflation fluids from the insufflation fluid source to the access member, and a third position corresponding to a closed operative state where the valve stem intersects the fluid passage to prevent egress of insufflation fluids from the access member, wherein the control valve is configured to rotate about an axis of rotation between the first, second, and third positions, the axis of rotation being parallel to the central longitudinal axis of the access member.

2. The access apparatus of claim 1 wherein the valve channel of the control valve is linear and is arranged about a valve channel axis.

3. The access apparatus of claim 2 wherein the valve intake port is configured to intersect the valve channel and is arranged about a valve intake port axis.

4. The access apparatus of claim 3 wherein the valve stem includes a closed side opposing the valve intake port along the valve intake port axis.

5. The access apparatus of claim 4 wherein the closed side of the valve stem is positioned radial outward of the chamber exit port of the fluid connector when in the first position of the control valve and intersects the flow passage of the fluid connector.

6. The access apparatus of claim 5 wherein the closed side of the valve stem is configured to close the chamber exit port of the valve chamber segment of the fluid connector when in the second position of the control valve.

7. The access apparatus of claim 6 wherein the closed side of the valve stem is positioned radial inward of the chamber exit port when in the third position of the control valve and intersects the flow passage of the fluid connector.

8. The access apparatus of claim 1 wherein the control valve includes a valve lever connected to the valve stem, the valve lever configured for manual manipulation and selectively movable to move the control valve between the first, second and third positions.

9. The access apparatus of claim 1 wherein the fluid connector and the access housing are monolithically formed.

10. The access apparatus of claim 1 including a closure element mounted relative to the access housing, the closure element configured to open upon introduction of the surgical object therethrough and close in the absence of the surgical object.

11. The access apparatus according to claim 10 wherein the fluid passage of the fluid connector is in fluid communication with the longitudinal opening of the access housing and the access member distal of the closure element.

12. An access apparatus, comprising:
   an access housing;
   an access member extending from the access housing, the access housing and the access member defining a central longitudinal axis and having a longitudinal opening for passage of a surgical object;
   a fluid connector mounted to the access housing and being configured for coupling to an insufflation fluid source, the fluid connector defining a fluid passage extending therethrough, the fluid connector defining a single exit port in a side wall portion thereof in fluid communication with the fluid passage; and
   a control valve at least partially positioned within the fluid connector, the control valve defining a valve channel therethrough and a valve intake port in fluid communication with the valve channel, the control valve selectively positionable between:
   a first position corresponding to a desufflation operative state where the valve intake port is aligned with the fluid passage of the fluid connector and the flow channel is aligned with the exit port of the fluid connector to permit insufflation fluids to flow from the access member through the valve intake port for discharge through the valve channel and the exit port;
   a second position corresponding to an insufflation operative state where the valve channel is aligned with the fluid passage of the fluid connector to permit passage of insufflation fluids from the insufflation fluid source through the fluid passage to the access member; and
   a third position corresponding to a closed operative state where the control valve intersects the flow passage of the fluid connector to prevent egress of insufflation fluids from the access member,
   wherein the control valve is configured to rotate about an axis of rotation between the first, second, and third positions, the axis of rotation being parallel to the central longitudinal axis of the access member.

13. The access apparatus of claim 12 wherein the fluid connector and the access housing are monolithically formed.

* * * * *